US012672779B2

(12) United States Patent
Krueger et al.

(10) Patent No.: US 12,672,779 B2
(45) Date of Patent: Jul. 7, 2026

(54) CAMERA BASED DETECTION OF SUBJECT POSITION

(71) Applicant: KONINKLIJKE PHILIPS N.V., Eindhoven (NL)

(72) Inventors: Sascha Krueger, Hamburg (DE); Julien Thomas Senegas, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/687,838

(22) PCT Filed: Sep. 5, 2022

(86) PCT No.: PCT/EP2022/074597
§ 371 (c)(1),
(2) Date: Feb. 29, 2024

(87) PCT Pub. No.: WO2023/036729
PCT Pub. Date: Mar. 16, 2023

(65) Prior Publication Data
US 2024/0350010 A1    Oct. 24, 2024

(30) Foreign Application Priority Data
Sep. 9, 2021    (EP) .................................... 21195748

(51) Int. Cl.
*A61B 5/00*        (2006.01)
*A61B 5/055*       (2006.01)

(52) U.S. Cl.
CPC .......... *A61B 5/0033* (2013.01); *A61B 5/0077* (2013.01); *A61B 5/055* (2013.01); *A61B 5/70* (2013.01)

(58) Field of Classification Search
None
See application file for complete search history.

(56) References Cited

U.S. PATENT DOCUMENTS

2005/0265516 A1*  12/2005  Haider ................... A61B 5/055
                                                              378/20
2006/0183997 A1*  8/2006  Haider ................. G01R 33/307
                                                              600/410
(Continued)

FOREIGN PATENT DOCUMENTS

CN        113116367 A      7/2021
EP         2726164 B1      9/2019
EP         3822845 A1      5/2021

OTHER PUBLICATIONS

Padilla et al."Collision Prediction Software for Radiotherapy Treatments" Med. Phys. 42(11) Nov. 2015 pp. 6448-6456.
(Continued)

*Primary Examiner* — Keith M Raymond
*Assistant Examiner* — Ashish S. Jasani

(57) ABSTRACT

Disclosed herein is a medical system (100, 300) comprising a memory (110) storing machine executable instructions (120) and an anatomical keypoint locator module (122). The anatomical keypoint locator module is configured to output a set of anatomical keypoint coordinates (126) of a subject (318) in response to receiving a camera image (124) descriptive of the subject. The medical system further comprises a computational system (104). Execution of the machine executable instructions causes the computational system to: receive (200) the camera image; receive (202) the set of anatomical keypoint coordinates in response to inputting the camera image into the anatomical keypoint locator module; receive (204) a list of coordinates (128); search (206) the list of coordinates to determine a match with the set of anatomical keypoint coordinates: and provide (208) a warning signal if the match is determined.

13 Claims, 7 Drawing Sheets

(56) References Cited

U.S. PATENT DOCUMENTS

| | | | |
|---|---|---|---|
| 2015/0092998 A1 | 4/2015 | Liu et al. | |
| 2016/0306924 A1 | 10/2016 | Singh et al. | |
| 2017/0205478 A1 * | 7/2017 | Brinker | A61B 5/1077 |
| 2022/0260656 A1 * | 8/2022 | Hatakenaka | A61B 5/704 |

OTHER PUBLICATIONS

G. Durbridge "Magnetic Resonance Imaging: Fundamental Safety Issues" Journal of the Orthopaedic and Sports Physical Therapy, vol. 41, No. 11 Nov. 1, 2011 p. 820-828.
International Search Report and Written Opinion from PCT/EP2022/074597 mailed Dec. 16, 2022.
Yang et al: "Body-loop related MRI radiofrequency-induced heating hazards: Observations, characterizations, and recommendations", Magnetic Resonance in Medicine, vol. 87, No. 1, Aug. 6, 2021 (Aug. 6, 2021) , pp. 337-348.

* cited by examiner

CAMERA BASED DETECTION OF SUBJECT POSITION

CROSS REFERENCE TO RELATED APPLICATIONS

This application is a U.S. national phase application of International Application No. PCT/EP2022/074597 filed on Sep. 5, 2022, which claims the benefit of EP Application Serial No. 21195748.5 filed on Sep. 9, 2021 and is incorporated herein by reference.

FIELD OF THE INVENTION

The invention relates to medical imaging, in particular to the automatic detection of a subject position or pose before imaging.

BACKGROUND OF THE INVENTION

Various medical imaging techniques such as Magnetic Resonance Imaging (MRI), Computed Tomography, Positron Emission Tomography, and Single Photon Emission Tomography enable detailed visualization of anatomical structure of a subject. In medical imaging modalities such as these, the proper placement of the subject prior to the procedure is critical. Otherwise the subject could be improperly imaged.

The journal publication Padilla et. al., "Collision prediction software for radiotherapy treatments," Med. Phys. 42 (11), November 2015, pp. 6448-6456, http://dx.doi.org/ 10.1118/1.4932628, discloses the use of a three-dimensional camera to scan the patient and immobilization devices in the treatment position at a simulator. The surface of the subject was reconstructed. The treatment isocenter was marked using simulated orthogonal lasers projected on the surface scan. The point cloud of this surface is then shifted to isocenter and converted from Cartesian to cylindrical coordinates. A slab was used to model a treatment couch. A cylinder with a radius equal to the normal distance from isocenter to the collimator plate, and a height defined by the collimator diameter was used to estimate collisions. Points within the cylinder clear through a full gantry rotation with the treatment couch at 0°, while points outside of it collide. The angles of collision are reported. This methodology was experimentally verified using a mannequin positioned in an alpha cradle with both arms up. Collision calculations were performed for the two treatment isocenters and the results compared to collisions detected the room. The accuracy of the three-dimensional surface was evaluated by comparing it to the external surface of the planning CT scan.

SUMMARY OF THE INVENTION

The invention provides for a medical system, a method and a computer program in the independent claims. Embodiments are given in the dependent claims.

The accurate detection of body position may be useful when performing a medical imaging scan of a subject. Currently systems exist that use a three-dimensional camera to image the surface of a subject. A disadvantage of these systems is that they may a do a poor job of predicting the pose of a subject. Embodiments may provide for an improved means of recognizing when a subject is positioned improperly or possibly placed in a hazardous pose before a medical imaging scan is performed. Embodiments may achieve this by using a anatomical keypoint locator module that provides a set of anatomical keypoint coordinates in response to receiving a camera image of the subject. The set of anatomical keypoint coordinates can be compared to a list of coordinates to determine, for example, if the absolute or relative position of individual anatomical keypoints is incorrect.

In one aspect the invention provides for a medical system that comprises a memory storing machine-executable instructions and an anatomical keypoint locator module. In some examples the anatomical keypoint locator module could be incorporated into the machine-executable instructions. The anatomical keypoint locator module is configured to output a set of anatomical keypoint coordinates of a subject in response to receiving a camera image descriptive of a subject.

An anatomical keypoint as used herein encompasses an anatomical landmark or position located in the subject. Anatomical keypoints could incorporate the locations of various joints or surface landmarks (eyes, cars, nose) of the subject. The camera image is descriptive of a subject and provides a description of the exterior or surface of the subject (texture and/or shape). For example, the camera image could be an optical image, an infrared image, thermal, or even a color image. In other examples the camera image is a three-dimensional surface image. In another example, the camera image is a composite image formed from multiple camera images. For example, two two-dimensional images could be used to provide a stereo image which provides three-dimensional or spatial information. In other examples the camera image is a composite image formed from multiple types of images. An infrared or thermal image could be combined with a three-dimensional image.

In both single or composite images, landmarks could be detected in each image. This could be used to provide additional information and options when matching anatomical keypoint coordinates to a list of coordinates. The identification of landmarks in multiple images may also enable the three-dimensional location of the landmarks.

The medical system further comprises a computational system. The computational system as used herein may encompass a computational system or processor that is possibly located at one or more locations. Execution of the machine-executable instructions causes the computational system to receive the camera image. Execution of the machine-executable instructions further causes the computational system to receive the set of anatomical keypoint coordinates in response to inputting the camera image into the anatomical keypoint locator module. Execution of the machine-executable instructions further causes the computational system to receive a list of coordinates.

The list of coordinates could take different forms in different examples. The list of coordinates could for example include the absolute or relative location of various anatomical keypoints of the subject. The list of coordinates could also define relationships between the anatomical keypoints. For example, in the case where it is an absolute position, the anatomical keypoints in the list of coordinates could specify locations which could provide data on a potential injury of the subject. For example, if the subject placed her or his appendage such as a hand, elbow or foot in a wrong location it may wind up in a collision or with being pinched when a subject is moved into a medical imaging system. An appendage as used herein refers to the hand or foot of a subject.

In some examples, the list of coordinates comprises two-dimensional coordinates. This may, for example, be used when the camera image is a two-dimensional image (such as when a color or infrared image is used). In other example the list of coordinates comprises three-dimensional coordinates. This may be the case when multiple two-dimensional camera images are used and/or when the camera image comprises a three-dimensional image.

In yet other examples, the list of coordinates comprises n-dimensional coordinates, where n is greater than three. This may be the case when coordinates are given in three-dimensions plus additional coordinates are used to measure their change in time. For example, three spatial dimensions and a temporal coordinate.

In other examples, if there is magnetic resonance imaging the touching of fingers or the touching of the fingers to particular body parts or even crossing arms or legs can result in a conductive loop within the body that can lead to RF heating of the subject. The position and pose of the subject can then be determined by defining a relationship between the position of the anatomical keypoints. For example, if the subject crosses her or his legs there will be a particular relationship in the coordinates. For example, the hips would be located next to each other and then there would be a crossing of the coordinates for the legs. The list of coordinates can therefore define a variety of positions and orientations of the subject.

Execution of the machine-executable instructions further causes the computational system to search the list of coordinates to determine a match with the set of anatomical keypoint coordinates. The determination of a match could take different forms in different examples. In example the determination is a detection of a match. For example, the list of coordinates could be searched to see if an appendage in the wrong location. In other cases, it could be searched to see whether appendages (such as the hands or feet) overlap or other body parts overlap forming a conductive loop. Execution of the machine-executable instructions further causes the computational system to provide a warning signal if the match is detected.

The determination of the match could also include an accuracy measure of how accurately the match fits to the set of anatomical keypoint coordinates. A match could be detected if the set of anatomical keypoint coordinates are within a certain distance or neighborhood of coordinates within the list of coordinates. However, within this neighborhood there may be better or worse matches. The accuracy measured could for example be a measure descriptive of the distance between the set of anatomical keypoint coordinates and the list of coordinates. This measure could be for example the RMS value of the difference between each coordinate.

In another embodiment the one or more conductive body loops are conductive loops within the body of the subject that can lead to RF heating of the subject. During the use of a magnetic resonance imaging systems there are large changing electromagnetic fields present. From Faraday's law it is known that a changing electromagnetic field will induce a current in a conductive loop. When a subject places a finger on a hip or other body part there is a chance that this touching will form an electrical connection between these two body regions thereby forming a conductive loop, this conductive loop is referred to herein as a conductive body loop. The current induced in this conductive body loop can cause resistive heating in the body of the subject leading that can result in a burn.

In another embodiment the list of coordinates define relative coordinates between two or more of the set of anatomical keypoint coordinates. The list of coordinates may contain sets of coordinates against which the anatomical keypoints are compared. For example the list of coordinates.

4 dinates may contain relative changes between different anatomical keypoint coordinates. The list of coordinates may also contain ratios of there relative changes.

The list of coordinates could have different sources. They could be received from a user interface, that is they could be entered by a user. In another example they could be predefined and could be received via a network interface or could be retrieved from a computer memory or storage device.

In another embodiment the list of coordinates comprises body poses defined as relative changes between the sets of anatomical keypoint coordinates. Then searching the list of coordinates to determine a match within the set of anatomical keypoint coordinates comprises detecting a body pose selected from body poses in the list of coordinates using the set of anatomical keypoint coordinates. In this embodiment the relative position of the anatomical keypoints is used to define particular body poses. Execution of the machine-executable instructions further causes the computational system to provide the warning signal if an irregular body pose is detected. This may be particularly useful in a situation where a certain positioning of the subject may lead to a bad medical imaging procedure or may place the subject in danger.

In another embodiment the list of coordinates comprises body poses defined as relative changes between members of the set of anatomical keypoint coordinates.

In another embodiment the detecting of a body pose selected from body poses in the list of coordinates using the set of anatomical keypoint coordinates comprises: determining the relative changes between the members of the set of anatomical keypoint coordinates, and comparing the relative changes between the members of the set of anatomical keypoint coordinates to the body poses.

In another embodiment the camera image comprises a three-dimensional surface image. For example, the camera image could have been acquired by a so-called three-dimensional camera. Detection of the body pose is at least partially performed using the three-dimensional surface image to detect limb positions. For example, the set of anatomical keypoint coordinates may be useful for defining the pose of the subject as well as the location of certain body parts. However, this information may not always provide detailed information which can be used to enhance the safety of the subject. For example, if the subject is going to be inserted into a medical imaging system the locations of the joints may not be sufficient to detect if a collision with the medical imaging system will occur when the subject is inserted. The three-dimensional surface image may also provide additional information as to the body pose and the outer dimensions of the subject.

In another embodiment detection of the body pose is at least partially performed using the three-dimensional surface image to detect limb locations by matching the three-dimensional surface image to a set of predetermined surface images each depicting a different body pose.

In another embodiment the set of anatomical keypoint coordinates comprises one or more appendage keypoint coordinates. For example, the anatomical keypoints which define the appendage can be provided on different levels. In some models the position of the wrists may be provided alone. In other examples details about the locations of various joints for various fingers may also be provided. Execution of the machine-executable instructions further causes the computational system to calculate a range of appendage coordinates for the one or more appendage keypoint coordinates. The set of anatomical keypoint coordinates may provide details not only on the location of various parts or the location of the wrist joint but may provide information on other joints such as the elbow and shoulder of the subject. This can be used to provide an estimate of the range of motion that the subject's append- ages may take during a medical procedure. This can then be used to predict if it is possible or likely that a subject will place her or his appendages in a dangerous position. The detection of the body pose can be determined by defining the body poses on the list of coordinates. This may be beneficial because it enables not only the detection of a particular body pose that is occurring when the image is taken, but also may be used for predicting if the subject will move into this body pose at a future point in time. This may be useful in improving not only the quality of medical imaging but also in improving patient safety.

In another embodiment the one or more appendage key- point coordinates are keypoint coordinates that define a location on an appendage of the subject.

In another embodiment the range of appendage coordi- nates is determined using a predefined range of allowable motions for the appendage keypoint coordinates. For example, the movement allowable by various joints of the body are known. These known possible or allowable move- ments can be espressed as a range of allowable motions for the appendage keypoint coordinates.

In another embodiment the medical system further com- prises a medical imaging system configured for acquiring medical imaging data from a subject at least partially within an imaging zone. The medical imaging in some examples may be a tomographic medical imaging such as an MRI. CT or PET system. In other examples the medical imaging system may include such things as an X-ray or a fluoroscopy system. The medical imaging system further comprises a subject support configured for supporting the subject at least partially within the imaging zone. The medical imaging system further comprises a camera system configured for acquiring the camera image descriptive of the subject on the subject support. That is to say the camera image is able to image the subject while she or he is being supported by the subject support. For example, the subject support may be a bed or couch which the subject lies on. Execution of the machine-executable instructions further causes the compu- tational system to control the camera system to acquire the camera image.

In another embodiment the camera system may have coordinates that are registered to the medical imaging sys- tem and/or the subject support. As an alternative to this, the anatomical keypoint locator module may also be configured for determining the coordinates with respect to the location on the subject support. For example, there may be an artificial intelligence module which is able to recognize the position of the subject relative to that of the subject support or of the medical imaging system and provide a registration between the coordinates system of the medical imaging system, the subject support and/or the camera system.

In another embodiment execution of the machine-execut- able instructions further causes the computational system to control the medical imaging system to acquire the medical imaging data.

In another embodiment execution of the machine-execut- able instructions further causes the computational system to reconstruct a medical image from the medical imaging data.

In another embodiment the camera system comprises an infra-red camera.

In another embodiment the camera system further com- prises an optical camera.

In another embodiment the optical camera is a color camera.

In another embodiment the medical imaging system is a thermal camera.

In another embodiment the medical imaging system com- prises a computed tomography system.

In another embodiment the medical imaging system com- prises a positron emission tomography system.

In another embodiment the medical imaging system com- prises a single photon emission tomography system.

In another embodiment the medical imaging system com- prises an image guided therapy system such as a gamma knife or LINAC guided by MRI or CT.

In another embodiment the medical imaging system com- prises a digital X-ray system.

In another embodiment the medical imaging system com- prises a digital fluoroscope.

In another embodiment the medical imaging system com- prises a magnetic resonance imaging system. The identifi- cation of the various poses for a magnetic resonance imag- ing system may be beneficial because it may be tricky or difficult for an operator to determine if the subject is in an improper or unsafe position.

In another embodiment the list of coordinates are config- ured to define one or more conductive body loops. This embodiment may be beneficial because the positioning of the body can cause conductive loops to be defined by the body. When the magnetic resonance imaging system is run, a current can be induced in one of these conductive body loops which may cause heating or RF burns in the subject. Defining conductive body loops in the list of coordinates may therefore improve the safety of a magnetic resonance imaging system.

In another embodiment execution of the machine-execut- able instructions further causes the computational system to provide a rendering of the camera image of an overlay descriptive of a match between the list of coordinates and the set of anatomical keypoint coordinates if the warning signal is provided. This may be beneficial because it may provide a visual guide for an operator of the medical imaging system and make it easier to put the subject in the proper position.

In another embodiment execution of the machine-execut- able instructions further causes the computational system to provide an audible warning system if the warning signal is provided. This may be an effective means of alerting an operator of the medical system if there is a problem.

In another embodiment execution of the machine-execut- able instructions further causes the computational system to render a warning message on a display if the warning signal is provided.

In another embodiment execution of the machine-execut- able instructions further causes the computational system to disable acquisition of the medical imaging data if the warning signal is provided. This may for example be par- ticularly useful in preventing an unsafe situation for the subject. In some examples once the position of the subject has changed the system may then enable the acquisition of the medical imaging data when the subject is then in a proper or safe position.

In another embodiment the list of coordinates is config- ured to define an insertion collision. For example, if the subject is placed on a subject support that is then inserted into the medical imaging system such as a magnet or CT ring it may be possible for the subject to collide with part of the medical imaging system as he or she is inserted.

In another embodiment the list of coordinates is config- ured to define a prohibited hand position. For example, if the subject places her or his hand in a location which may result in the hand possibly being pinched. This may also be a position where the hand is touching an apparatus or device which the subject should not touch.

In another embodiment the list of coordinates is configured to define a prohibited foot position. As with the hand the foot may be placed in a position where it may become pinched or placed in an improper location (e.g. forming a conductive body loop).

In another embodiment the list of coordinates is configured to define a medical apparatus location. There may for example be various coils or other fixtures or apparatuses which are in the vicinity of the subject. The system can then be used to prevent the possibility of the subject touching or modifying the medical apparatus.

In another embodiment the list of coordinates is configured to define a subject support pinch point. This for example may be locations where if a portion of the subject is touching the subject may be pinched.

In another embodiment the list of coordinates is configured to define locations of high electric or magnetic fields which may be involved in creating high local SAR exposure for magnetic resonance imaging.

In another embodiment the medical system is used with an X-ray system, a digital fluoroscope, or a computed tomography system. The list of coordinates is configured to define locations that will receive unnecessary X-ray. For example, when the eyes are in the X-ray plane for a head CT scan. Or the hands lay on the abdomen for an abdomen scan. The list of coordinates can then be used to avoid or minimize the amount of radiation that these body regions receive.

In another embodiment the anatomical keypoint locator module comprises a neural network configured to output a separate anatomical keypoint coordinate probability map for each of the at least one anatomical keypoint coordinates in response to receiving the image of the subject on the subject support. For example, various joints and locations within the subject may be included in the anatomical keypoint coordinates. For each of the set there may be a separate image or map which is output and the probability of the joint or anatomical location being in a particular position is output on this map. The most likely position can for example be obtained by taking the maximum probability. This system may be particularly good at identifying the location of joints or other anatomical locations when they are obscured or partially obscured. For example, if the subject has clothing or a blanket placed on the subject.

Execution of the machine-executable instructions further causes the computational system to receive the separate anatomical keypoint coordinate probability map in response to inputting the image into the neural network. Execution of the machine-executable instructions further causes the computational system to calculate the set of anatomical keypoint coordinates from the separate joint coordinate probability map for each of the set of joint coordinates.

The training of the neural network may be achieved by having images of the subject and then having training keypoint coordinate probability maps for each of the at least one anatomical keypoint coordinates that are labeled. For example, one could have a series of images of different subjects in slightly different positions wearing different clothing or even being covered with blankets or having the body partially obscured. An operator could then go and mark up various points so that the locations of the anatomical keypoint coordinates are indicated. This can then be used for example in a deep learning algorithm to train the neural network.

In another embodiment the list of coordinates comprises a predetermined list of coordinates stored in the memory.

In another aspect the invention provides for a method of medical imaging. The method comprises receiving a camera image. As was mentioned above the camera image can be a composite image that comprises multiple images as well as possibly multiple types of images. The method further comprises receiving a set of anatomical keypoint coordinates in response to inputting the camera image into an anatomical keypoint locator module. The anatomical keypoint locator module is configured to output a set of anatomical keypoint coordinates of a subject in response to receiving a camera image descriptive of the subject. The method further comprises receiving a list of coordinates. The method further comprises searching the list of coordinates to determine a match with the set of anatomical keypoint coordinates. The method further comprises providing a warning signal if the match is determined.

In another aspect the invention provides for a computer program comprising machine-executable instructions for execution by a computational system. For example, the computer program may be stored on a non-transitory storage medium. Execution of the machine-executable instructions causes the computational system to receive the camera image. Execution of the machine-executable instructions further causes the computational system to receive the set of anatomical keypoint coordinates in response to inputting the camera image into the anatomical keypoint locator module. Execution of the machine-executable instructions further causes the computational system to receive a list of coordinates. Execution of the machine-executable instructions further causes the computational system to search the list of coordinates to determine a match with the set of anatomical keypoint coordinates. Execution of the machine-executable instructions further causes the computational system to provide a warning signal if the match is determined.

In another embodiment the memory further stores an object detection module. The object detection module may be a software module that is able to identify objects and or critical object locations in an image. For example, the object detection module may be a convolutional neural network used to identify objects such as equipment, trolleys, injectors, docking points, or other pinch point locations. In some examples the locations where a subject could for example possibly pinch fingers. The object detection module could provide a list of object coordinates that could be appended to the list of coordinates.

The object determination module could be a standard convolutional neural network that is used to classify images and put bounding boxes within an image. The objected determination module could be trained using deep learning with training images that are labeled with either objects and/or pinch point locations.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit." "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid state hard disk, flash memory, USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object-oriented programming language such as Java, Python, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a computational system of a general purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus. IEEE 1394 port, parallel port, IEEE 1284 port, serial port, RS-232 port, IEEE-488 port, Bluetooth connection. Wireless local area network connection, TCP/IP connection. Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical imaging data is defined herein as being recorded measurements made by a tomographic medical imaging system descriptive of a subject. The medical imaging data may be reconstructed into a medical image. A medical image id defined herein as being the reconstructed two- or three-dimensional visualization of anatomic data contained within the medical imaging data. This visualization can be performed using a computer.

Medical imaging data is defined herein as the measurements made by a medical imaging system. The medical imaging data may be reconstructed into a medical image which is descriptive of a subject.

K-space data is defined herein as being the recorded measurements of radio frequency signals emitted by atomic spins using the antenna of a Magnetic resonance apparatus during a magnetic resonance imaging scan. Magnetic resonance data is an example of medical image data.

A Magnetic Resonance Imaging (MRI) image or MR image is defined herein as being the reconstructed two- or three-dimensional visualization of anatomic data contained within the magnetic resonance imaging data and is an example of a medical image. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF EMBODIMENTS

Like numbered elements in these figures are either equivalent elements or perform the same function. Elements which have been discussed previously will not necessarily be discussed in later figures if the function is equivalent.

Figure 1:
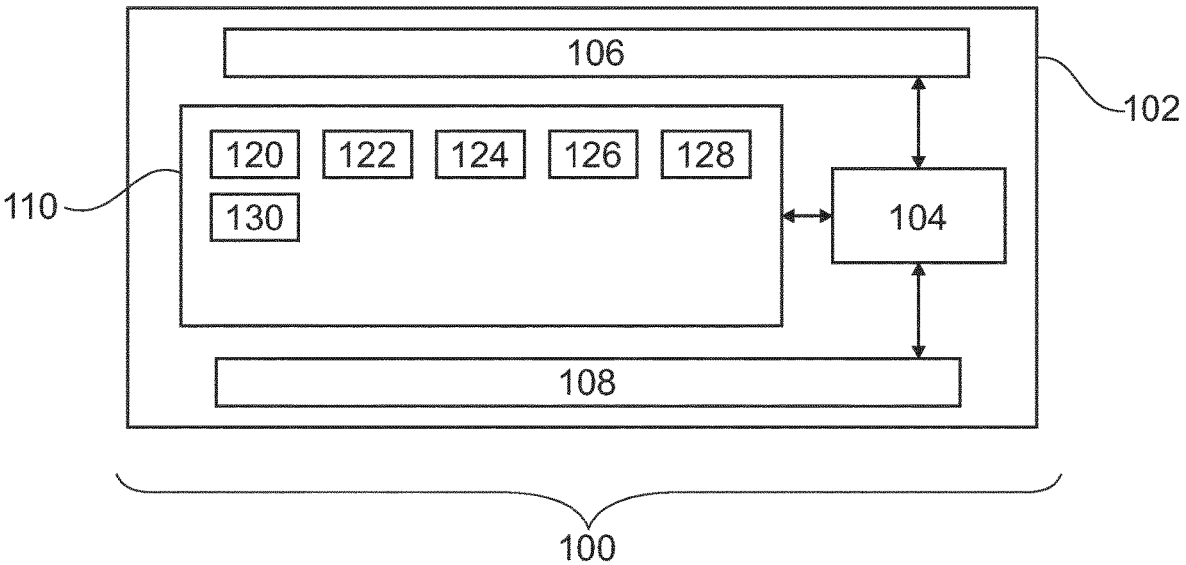
FIG. 1 illustrates an example of a medical system.

FIG. 1 illustrates an example of a medical system 100. The medical system 100 is shown as being comprised of a computer 102. The computer 102 is intended to represent one or more computers or computational devices at one or more locations. For example, the computer 102 could be integrated into a medical imaging system such as a magnetic resonance imaging system. In other examples the medical system 100 could be a workstation, for example, in a radiology department. In yet other examples the medical system 100 could be a server configured for performing image processing tasks for a radiology department. In yet another example the medical system 100 could be implemented as a web-based service that is provided. For example, the computer 102 could be a virtual computing system.

The computer 102 is shown as comprising a computational system 104 which may represent one or more computational systems or processors located at one or more locations. The computational system 104 is connected to an optional hardware interface 106. If there are other components of the medical system 100 such as a medical imaging system, the hardware interface 106 may enable the computational system 104 to communicate with these other components. The computational system 104 is further shown as being connected to an optional user interface 108. The user interface 108 may provide for example displays or human interface devices which enable the operator to control the operation and function of the medical system 100.

The computational system 104 is further shown as being connected to a memory 110. The memory 110 represents the various types of memory such as a hard drive, RAM or non-transitory storage medium that could be in communication with the computational system 104. The memory 110 is shown as containing machine-executable instructions 120. The machine-executable instructions 120 enable the computational system 104 to perform various computational and data processing tasks. The machine-executable instructions 120 may also enable the computational system 104 to control other components of the medical system 100 also.

The memory 110 is further shown as containing an anatomical keypoint locator module 122. The anatomical keypoint locator module 122 may for example be implemented as a neural network that takes a camera image 124 as input and outputs a set of anatomical keypoint coordinates. The memory 110 is further shown as storing a camera image 124 and a set of anatomical keypoint coordinates 126. The memory 110 is further shown as containing a list of coordinates 128. The list of coordinates 128 may for example be a list of absolute coordinates or they may be pairs or definitions of relative coordinate positions. This for example could be used to identify dangerous poses or positions of the subject which are not desirable. The memory 110 is further shown as containing a warning signal which may be provided if the set of anatomical keypoint coordinates 126 matches the list of coordinates 128.

Figure 2:
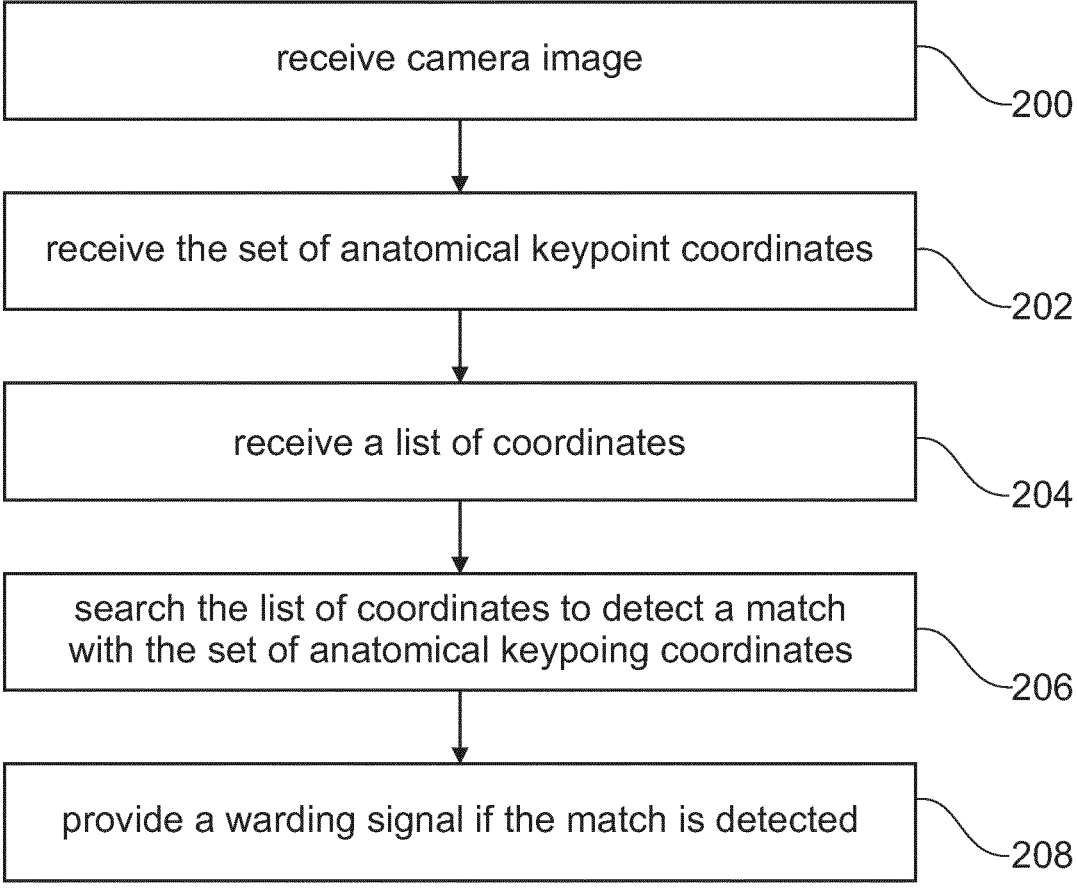
FIG. 2 shows a flow chart which illustrates a method of using the medical system of FIG. 1.

FIG. 2 shows a flowchart which illustrates a method of operating the medical system 100 of FIG. 1. First, in step 200, the camera image 124 is received. Next, in step 202, the set of anatomical keypoint coordinates 126 are received from the anatomical keypoint locator module 122 in response to receiving the camera image 124 as input. Next, in step 204, a list of coordinates 128 is received. In some examples the list of coordinates 128 could be received from the user interface 108. In other examples they could be retrieved from the memory 110. Next, in step 206, the list of coordinates 128 is searched to determine a match with the set of anatomical keypoint coordinates 126. Finally, in step 208, the warning signal 130 is provided if a match is determined.

Figure 3:
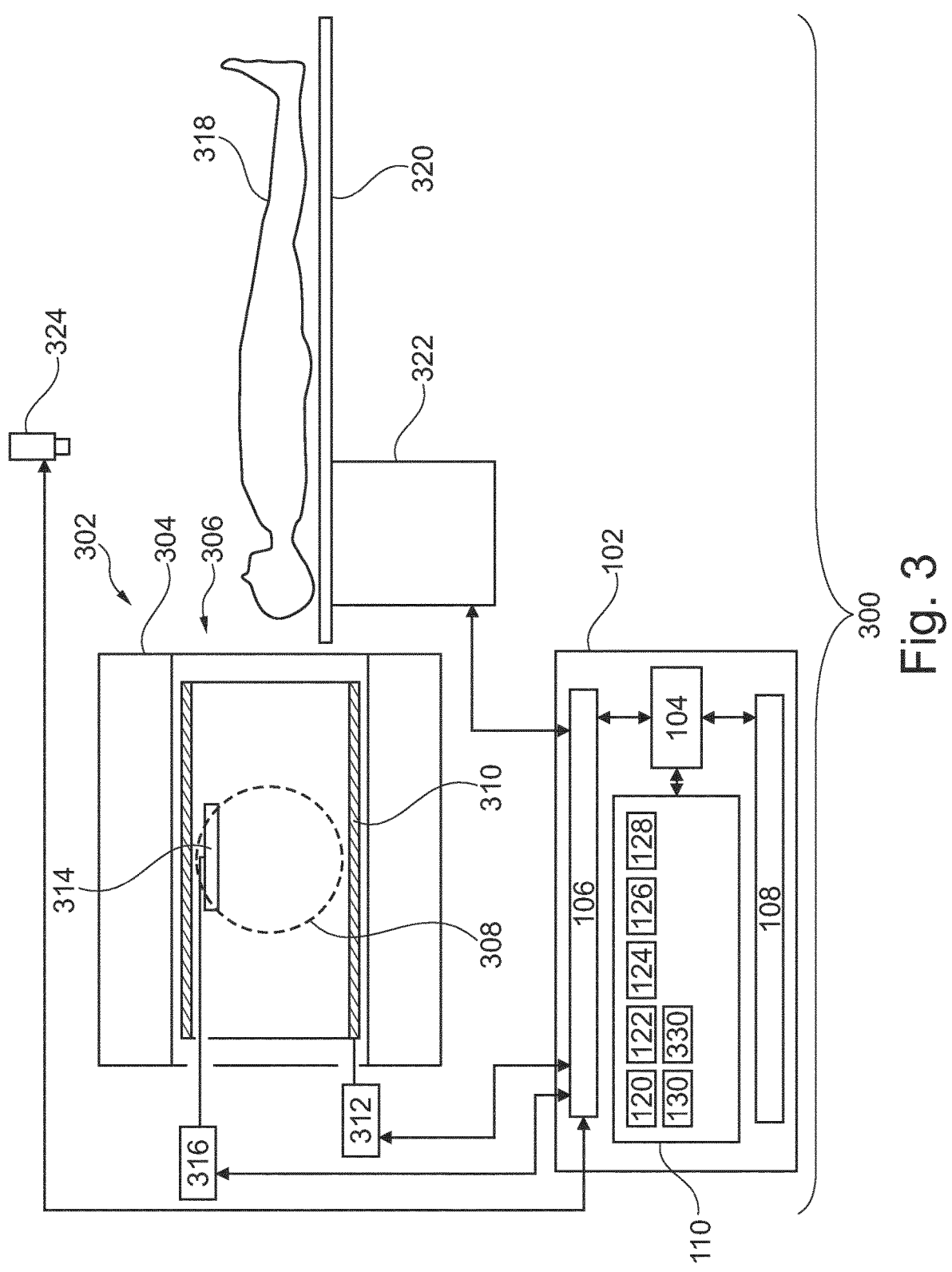
FIG. 3 illustrates a further example of a medical system.

FIG. 3 illustrates a further example of a medical system 300. The medical system 300 is similar to the medical system 100 depicted in FIG. 1 except that it additionally comprises a magnetic resonance imaging system 304 and a camera system 324.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 306 of the cylindrical magnet 304 there is an imaging zone 308 where the magnetic field is strong and uniform enough to perform magnetic resonance imaging. The magnetic resonance data that is acquired typically acquired for the field of view. A subject 318 is shown as being supported by a subject support 320 in view of a camera 322.

The camera 322 is shown as being position so that the subject 318 can be imaged when reposing on the subject support 320. The subject support 320 is shown as being connected to an actuator 322 which is configured for inserting the subject support 320 and the subject 318 into the bore 306 of the magnet 304.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

The subject 318 and the subject support 320 are shown in this Fig. as being outside of the bore 306 of the magnet 304. While the subject is in this position the camera system 324 is positioned to image an external surface of the subject 318. This may be used to provide the camera image 124. The camera system 324 could for example be comprised of an optical camera, a color camera, an infra-red camera, and/or 3D camera. The camera system 324 could also be placed within the bore of the magnet 306 also.

The hardware interface 106 is shown as being connected to the camera system 324, the actuator 322, the magnetic field gradient coil power supply 312 and the transceiver 316. The computational system 104 is able to control these and other components via the hardware interface 106.

The memory 110 is further shown as containing pulse sequence commands 330. The pulse sequence commands are commands or data which may be converted into such commands which may be used to control the magnetic resonance imaging system to acquire magnetic resonance data. The magnetic resonance data may be reconstructed into a magnetic resonance image. The magnetic resonance data is an example of medical imaging data and a magnetic resonance image is an example of a medical image.

Figure 4:
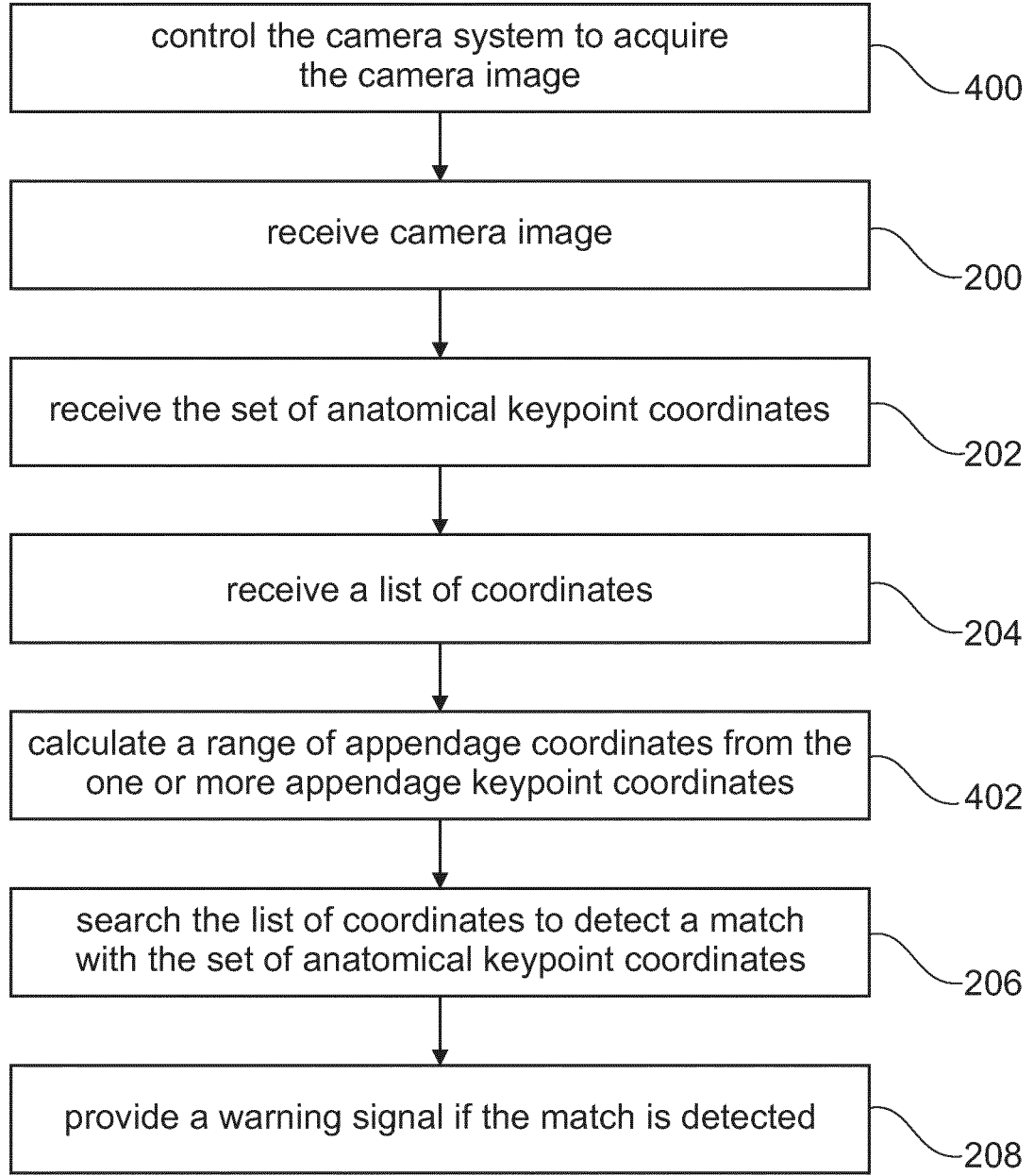
FIG. 4 shows a flow chart which illustrates a method of using the medical system of FIG. 3.

FIG. 4 shows a flowchart which illustrates a method of operating the medical system 300 of FIG. 3. The method illustrated in FIG. 4 is similar to the method illustrated in FIG. 2. In FIG. 4 the method begins with step 400. In step 400 the computational system 104 controls the camera system 324 to acquire the camera image 124. After step 400 is performed steps 200, 202, and 204 as are illustrated in FIG. 2 are performed. After step 204 is performed step 402 is performed. In step 402 a range of appendage coordinates are calculated from one or more appendage keypoint coordinates. An appendage as used herein is a hand or foot. So by determining one or more keypoint coordinates which indicate a coordinate on a hand or foot a range of coordinates for the hand or foot are calculated. This enables the prediction of the likely positions the subject will put her or his hand into during an examination.

After step 402 is performed, step 206 is performed. In this case the list of coordinates is searched to determine if a particular body pose is detected. The particular body pose is defined by a relative position of various keypoint coordinates. In this case for example, if it indicates it is possible that fingertips may touch or if the legs may be crossed. These are two particular examples. After step 206 is performed, step 208 is performed as was illustrated in FIG. 2.

Preparing a patient for a Magnetic Resonance (MR examination), or other imaging modality) may be a time-consuming task and may require trained skills of the operator. The operator may place surface coils on or adjacent to the anatomy to be imaged. The patient setup tends to be complex and includes blankets, cushions, hearing protection, nurse call. While completing all these tasks proper patient pose needs to be ensured for safe Magnetic Resonance Imaging (MRI) scanning. One of the most important things to avoid are body loops which may represent current paths for the induced Radio Frequency (RF) currents which may in turn lead to increased local electric field and Specific Absorption Ratio (SAR) resulting in potential harm to the patient in form of RF burns.

Against this background a patient setup surveillance workflow-analyzing camera (camera system 324) is proposed that analyzes the position and orientation of the patient's limbs even when partly covered by blankets or coils. Such a camera can estimate the risk of looping or touching body parts that have highest probability of leading to safety-relevant body poses, e.g. like touching hands or looping arms or legs. The camera will run algorithms to detect position and orientation of the patient body joints and limbs. From this the patient size is known and also the direction and (potentially touching) endpoints of the partly hidden limbs can be estimated.

Figure 5:
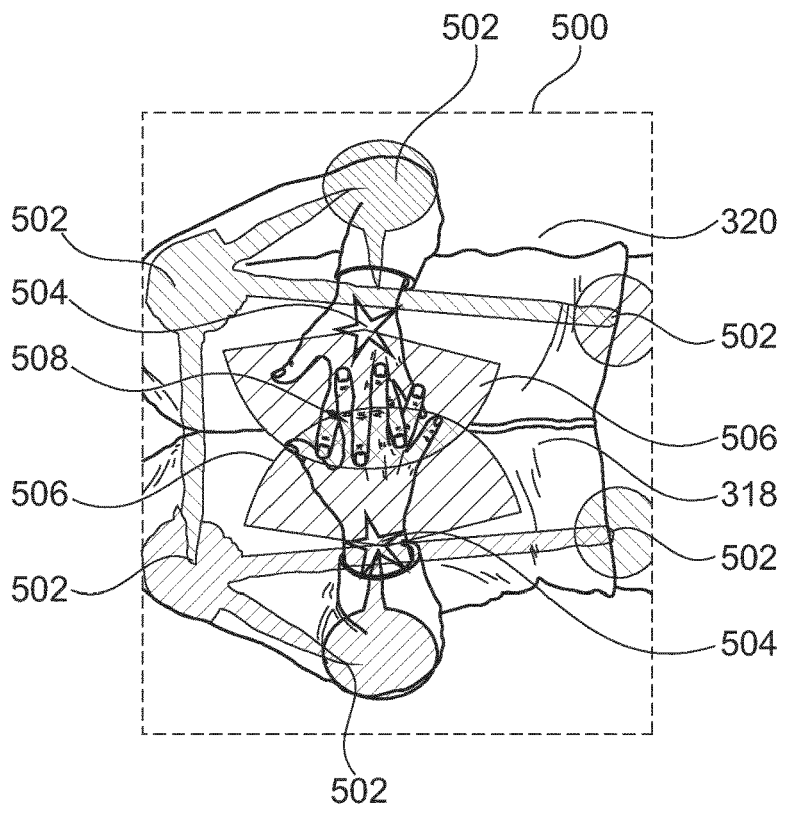
FIG. 5 shows an example for an arm pose that has a high likelihood of allowing the hands to touch

FIG. 5 shows an example of a camera image 502 that has the set of anatomical keypoint coordinates 126 superimposed upon it. Within the image the subject 318 reposing on the subject support 320 is visible. A number of the anatomical keypoints 502 of the set of anatomical keypoints is visible. The set of anatomical keypoints also includes the wrist keypoint coordinates 504. The wrist keypoint coordinates are an example of an appendage keypoint coordinate or a hand keypoint coordinate. The wrist keypoint coordinate 504 defines the position of the subject's hands. From this a range of hand coordinates 506 has been calculated and is displayed. This shows the possible positions which the subject 318 could put her or his fingers into. In this example the range of hand coordinates 506 overlap and touching fingers 508 are visible. For a magnetic resonance imaging examination this would provide a ground loop between the subject's two arms and chest. This could lead to RF heating at the subject's fingertips that are touching 508. FIG. 5 shows an example for an arm pose that has a high likelihood of allowing the hands to touch for the given subject. In this configuration, a body loop can occur and the risk of RF burns is high. In such a situation the tech should be alarmed and the arm pose should be corrected such that physical contact between the two hands is no longer possible.

Figure 6:
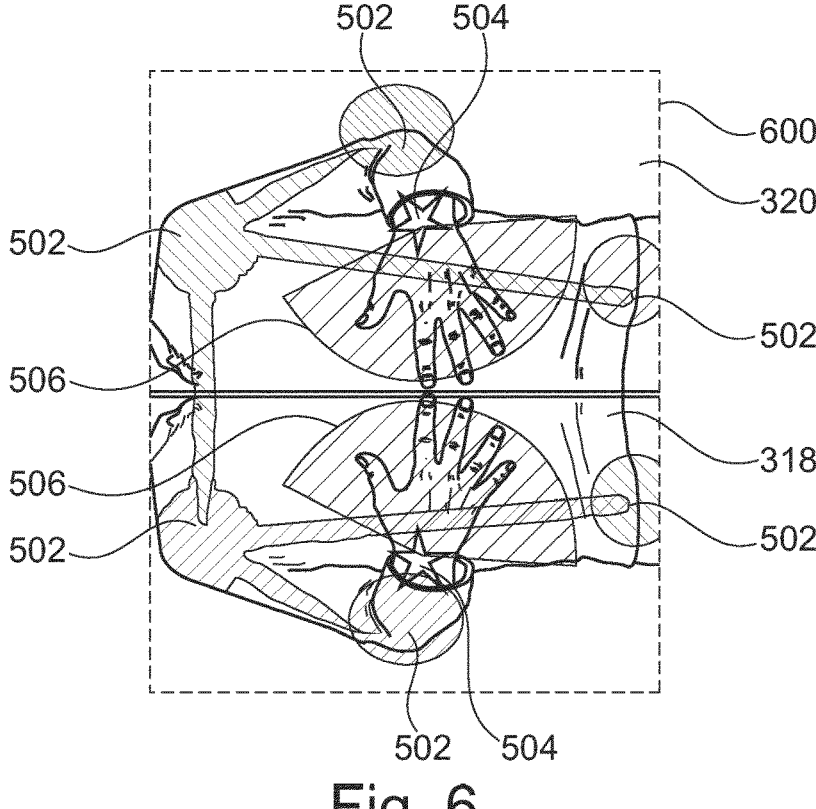
FIG. 6 shows a pose where the hands are close but the fingers are less likely to touch than in FIG. 5.

FIG. 6 shows an image of the same subject 318 reposing on the same subject support 320. In this example the subject's hands are in a different location and it is visible the range of hand coordinates 506 are no longer overlapping. As such, the subject's 318 fingers are not touching. In this example the possibility of a conductive body loop has been eliminated. FIG. 6 shows the threshold situation where the hands are close but the fingers may or may not touch. This situation may possibly represent a high risk for RF burns and therefore the tech could be warned.

Figure 7:
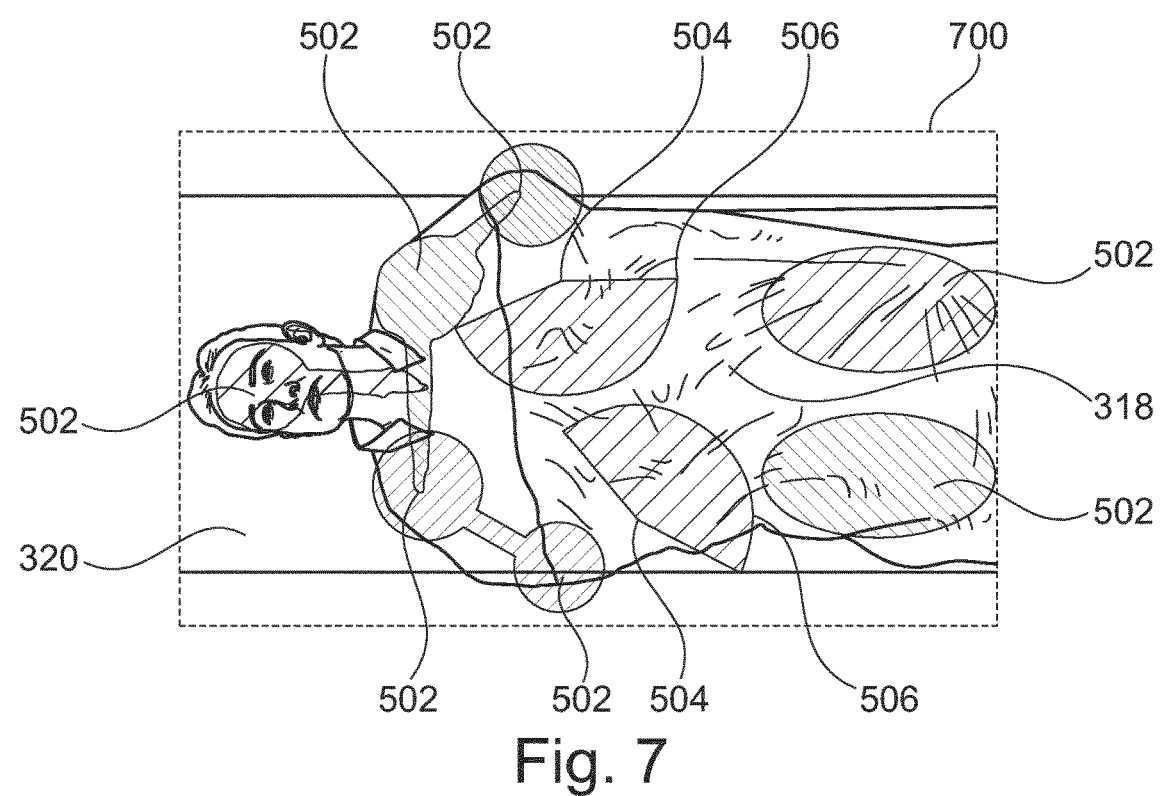
FIG. 7 shows a similar situation as illustrated in FIG. 6 with a blanket obscuring the arms and hands.

FIG. 7 illustrates a further example of a camera image with the set of anatomical keypoints 502, 504 superimposed on the image 700. The subject is partially covered with a blanket. The wrist keypoint coordinates 504 are again identified as is the range of hand coordinates 506. In this example the range of hand coordinates are not overlapping. FIG. 7 shows a similar situation with a blanket obscuring the arms. In all 3 images, the color overlays represent the computed probability maps for the joints and limbs and the yellow half-circles show the estimated possible movement range. The camera will detect such situations with residual risk of unsafe situations.

Figure 8:
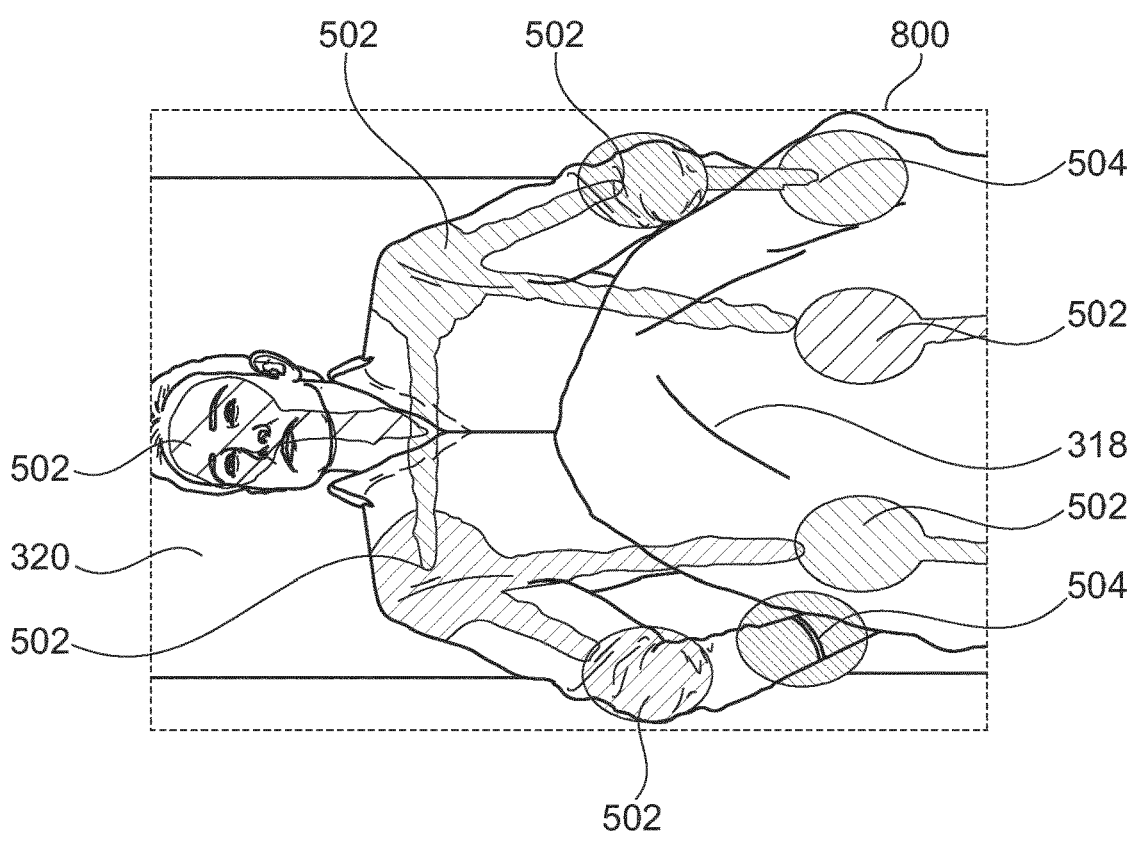
FIG. 8 shows an example of a pose which may be preferable from an RF perspective for a magnetic resonance imaging procedure.

FIG. 8 shows a further example of a camera image 800. In this example the anatomical keypoints 502, 504 are still shown. The hands are sufficiently far apart that there is no need to display or show the range of hand coordinates. The image 800 illustrates an example of a safe pose for the subject 318 during a magnetic resonance imaging examination. FIG. 8 shows an example of a pose which may be preferable from an RF perspective.

Figure 9:
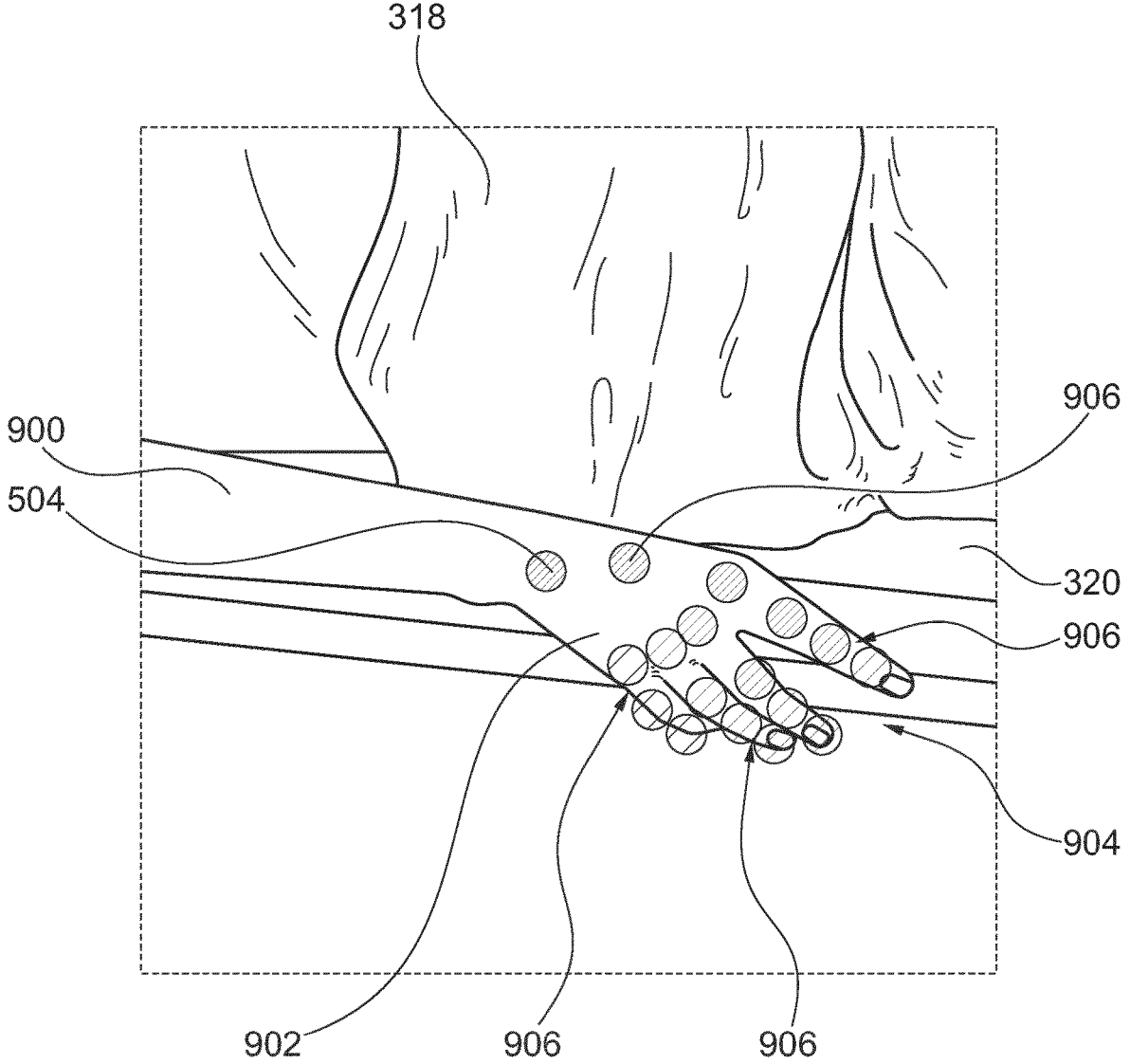
FIG. 9 shows a subject reposing on a subject support with a zoomed view of an arm and a hand.

FIG. 9 shows an image of a subject 318 reposing on a subject support 320. This image zooms to show the arm 900 and hand 902 of the subject in more detail. The wrist anatomical keypoint 504 is visible. In addition, there are a large number of finger anatomical keypoints 906 which indicated the location of finger joints and the finger tips are visible. The subject support 320 has a sliding mechanism which moved it and the side of the subject support 904 is potential pinch point or location where the subject 318 could potentially pinch a finger. The entire side region 904 may be identified as a potential pinch point.

The identification of the finger anatomical keypoints 906 enables the determination if a finger could potentially be injured by the sliding mechanism. This enables the detection of a safety risk caused by the hand 902 grabbing around the table edge or side region 904. This risk is immediately visible and would be detected by comparing with the coordinate lists. Also, if partial occlusions of the hand 902 occur, it may still be possible to predict the location of the finger anatomical keypoints.

A possible example is described here. The camera system 324 is streaming images to the processing unit (computational system 104) during patient setup. The position of the body joints is detected automatically by a detection algorithm. This algorithm computes spatial probability maps of joint presence. Alternatively, the segments connecting two joints can be directly detected (the limbs thereafter). Based on the size and the orientation of the body segments a region representative of the likelihood of the presence is computed. In case the camera is also providing 3D data (e.g. in form of a depth map), these additional data can be used to refine the computation of the body part presence regions. If the computed regions overlap or are very close to each other, the pose configuration is flagged as potentially hazardous incl. localization info to guide the operator to solve the conflict.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

REFERENCE SIGNS LIST 100 medical system
102 computer
104 computational system
106 hardware interface
108 optional user interface
110 memory
120 machine executable instructions
122 anatomical keypoint locator module
124 camera image
126 set of anatomical keypoint coordinates
128 list of coordinates
130 warning signal
200 receive the camera image
202 receive the set of anatomical keypoint coordinates in response to inputting the camera image into the anatomical keypoint locator module
204 receive a list of coordinates
206 search the list of coordinates to detect a match with the set of anatomical keypoint coordinates
208 provide a warning signal if the match is detected
300 medical system
302 magnetic resonance imaging system
304 magnet
306 bore of magnet
308 imaging zone
310 magnetic field gradient coils
312 magnetic field gradient coil power supply
314 radio-frequency coil
316 transceiver
318 subject
320 subject support
322 actuator
324 camera system
330 pulse sequence commands
400 control the camera system to acquire the camera image
402 calculate a range of appendage coordinates from the one or more appendage keypoint coordinates
500 camera image
502 anatomical keypoint
504 wrist (appendage or hand) keypoint coordinate
506 range of hand (appendage) coordinates
508 touching fingers 600 camera image
700 camera image
800 camera image
900 arm
902 hand
904 pinch location or pinch point
906 finger keypoint coordinates

The invention claimed is:

1. A medical system comprising:
a memory storing machine executable instructions and an anatomical keypoint locator module, wherein the anatomical keypoint locator module is configured to output a set of anatomical keypoint coordinates of a subject in response to receiving a camera image descriptive of the subject;
a medical imaging system configured to acquire medical imaging data from a subject at least partially within an imaging zone, wherein the medical imaging system comprises a magnetic resonance imaging system;
a subject support configured to support the subject at least partially within the imaging zone; and
a camera system configured to acquire the camera image descriptive of the subject on the subject support;
a computational system, wherein execution of the machine executable instructions causes the computational system to:
control the camera system to acquire the camera image;
receive the camera image;
receive the set of anatomical keypoint coordinates in response to inputting the camera image into the anatomical keypoint locator module;
receive a list of coordinates, wherein the list of coordinates is configured to define one or more conductive body loops that include at least one of an insertion collision, a prohibited hand position, a prohibited foot position, a medical apparatus location, or a subject support pinch point;
search the list of coordinates to determine a match with the set of anatomical keypoint coordinates; and
provide a warning signal if the match is determined.

2. The medical system of claim 1, wherein the list of coordinates comprises body poses defined as relative changes between the set of anatomical keypoint coordinates, wherein the searching of the list of coordinates to determine a match with the set of anatomical keypoint coordinates comprises detecting a body pose selected from body poses in the list of coordinates using the set of anatomical keypoint coordinates, wherein execution of the machine executable instructions further causes the computational system to provide the warning signal if the body pose is detected.

3. The medical system of claim 2, wherein the list of coordinates comprises body poses defined as relative changes between members of the set of anatomical keypoint coordinates, wherein detecting a body pose selected from body poses in the list of coordinates using the set of anatomical keypoint coordinates comprises:
determining the relative changes between the members of the set of anatomical keypoint coordinates, and
comparing the relative changes between the members of the set of anatomical keypoint coordinates to the body poses.

4. The medical system of claim 1 wherein the camera image comprises a three-dimensional surface image, wherein detection of the body pose is at least partially performed using the three-dimensional surface image to detect limb locations, and wherein detection of the body pose is at least partially performed using the three-dimensional surface image to detect limb locations by matching the three-dimensional surface image to a set of predetermined surface images each depicting a different body pose.

5. The medical system of claim 2 wherein the set of anatomical keypoint coordinates comprises one or more appendage keypoint coordinates, wherein execution of the machine executable instructions further causes the computational system to calculate a range of appendage coordinates from the one or more appendage keypoint coordinates, wherein detection of the body pose selected from the body poses in the list of coordinates is performed using the range of appendage coordinates.

6. The medical system of claim 5, wherein the one or more appendage keypoint coordinates are keypoint coordinates located on an appendage of the subject and/or wherein the range of appendage coordinates is determined using a predefined range of allowable motions for the appendage keypoint coordinates.

7. The medical system of claim 1, wherein the medical imaging system further comprises any one of the following: a computed tomography system, a positron emission tomography system, a single photon emission tomography system, and an image guided radiotherapy system.

8. The medical system of claim 1, wherein execution of the machine executable instructions further causes the computational system to perform at least one of a group consisting of the following if the warning signal is provided:

provide a rendering of the camera image with an overlay descriptive of the match between the list of coordinates and the set of anatomical keypoint coordinates;

provide an audible warning signal, render a warning message on a display, or disable acquisition of the medical imaging data.

9. The medical system of claim 1, wherein the anatomical keypoint locator module comprises a neural network configured to output a separate anatomical keypoint coordinate probability map for each set of the anatomical keypoint coordinates in response to receiving the image of the subject on the subject support, wherein execution of the machine executable instructions further causes the computational system to:

receive the separate anatomical keypoint coordinate probability map in response to inputting the image into the neural network; and calculate the set of anatomical keypoint coordinates from the separate anatomical keypoint coordinate probability map for each set of the anatomical keypoint coordinates.

10. The medical system of claim 1, wherein the list of coordinates comprises a predetermined list of coordinates stored in the memory.

11. The medical system of claim 1, wherein the one or more conductive body loops are conductive loops within the body of the subject that can lead to RF heating of the subject and/or wherein the list of coordinates define relative coordinates between two or more of the set of anatomical keypoint coordinates.

12. A method of medical imaging, wherein the method comprises:

controlling a camera system to acquire a camera image, wherein the camera image is descriptive of a subject on a subject support, wherein the subject support is configured to support the subject at least partially within an imaging zone of a medical imaging system, wherein the medical imaging system is configured for acquiring medical imaging data from the subject at least partially within the imaging zone, wherein the medical imaging system comprises a magnetic resonance imaging system;

receiving a camera image;

receiving a set of anatomical keypoint coordinates in response to inputting the camera image into an anatomical keypoint locator module, wherein the anatomical keypoint locator module is configured to output the set of anatomical keypoint coordinates of the subject in response to receiving the camera image descriptive of the subject;

receiving a list of coordinates, wherein the list of coordinates is configured to define one or more conductive body loops that include at least one of an insertion collision, a prohibited hand position, a prohibited foot position, a medical apparatus location, or a subject support pinch point;

searching the list of coordinates to determine a match with the set of anatomical keypoint coordinates; and providing a warning signal if the match is determined.

13. A non-transitory computer-readable medium that stores a computer program comprising machine executable instructions and an anatomical keypoint locator module for execution by a computational system, wherein the anatomical keypoint locator module is configured to output a set of anatomical keypoint coordinates of a subject in response to receiving a camera image descriptive of the subject, wherein the computational system is configured to control a medical system, wherein the medical system comprises:

a medical imaging system configured to acquire medical imaging data from the subject at least partially within an imaging zone, wherein the medical imaging system comprises a magnetic resonance imaging system;

a subject support configured to support the subject at least partially within the imaging zone; and a camera system configured to acquire the camera image descriptive of the subject on the subject support wherein execution of the machine executable instructions causes the computational system to:

control the camera system to acquire the camera image;

receive the camera image;

receive the set of anatomical keypoint coordinates in response to inputting the camera image into the anatomical keypoint locator module;

receive a list of coordinates, wherein the list of coordinates is configured to define one or more conductive body loops that include at least one of an insertion collision, a prohibited hand position, a prohibited foot position, a medical apparatus location, or a subject support pinch point;

search the list of coordinates to determine a match with the set of anatomical keypoint coordinates; and provide a warning signal if the match is determined.

* * * * *